(12) United States Patent
Kimura et al.

(10) Patent No.: US 7,037,649 B2
(45) Date of Patent: May 2, 2006

(54) IMMOBILIZED NUCLEIC ACID AND METHOD FOR DETECTING NUCLEIC ACID

(75) Inventors: Naoki Kimura, Chiba (JP); Tatsuo Ichihara, Chiba (JP); Shogo Moriya, Chiba (JP)

(73) Assignee: Nisshinbo Industries, Inc., Tokyo (JP)

( * ) Notice: Subject to any disclaimer, the term of this patent is extended or adjusted under 35 U.S.C. 154(b) by 0 days.

(21) Appl. No.: 09/771,043

(22) Filed: Jan. 26, 2001

(65) Prior Publication Data

US 2002/0018996 A1 Feb. 14, 2002

(30) Foreign Application Priority Data

Jan. 26, 2000 (JP) .............................. 2000-021843

(51) Int. Cl.
- C12Q 1/68 (2006.01)
- C12P 19/34 (2006.01)
- C07H 21/00 (2006.01)
- C07H 21/02 (2006.01)
- C12M 1/34 (2006.01)

(52) U.S. Cl. .................... 435/6; 435/7.1; 435/91.1; 435/91.2; 435/287.2; 536/22.1; 536/23.1; 536/24.3; 536/24.33

(58) Field of Classification Search .............. 435/6, 435/7.1, 91.1, 91.2, 287.2; 536/22.1, 23.1, 536/24.3–24.33
See application file for complete search history.

(56) References Cited

U.S. PATENT DOCUMENTS

| | | | |
|---|---|---|---|
| 5,683,875 A * | 11/1997 | Lichtenwalter ............ | 435/6 |
| 5,919,626 A * | 7/1999 | Shi et al. .................. | 435/6 |
| 5,932,711 A | 8/1999 | Boles et al. | |
| 5,981,734 A | 11/1999 | Mirzabekov et al. | |
| 6,210,894 B1 * | 4/2001 | Brennan ..................... | 435/6 |
| 6,221,635 B1 * | 4/2001 | Rovera et al. | |
| 6,506,895 B1 * | 1/2003 | Guire et al. ............. | 536/25.32 |
| 6,815,212 B1 * | 11/2004 | Ness et al. ............... | 436/173 |
| 2004/0023226 A1 | 2/2004 | Ozkan | |

FOREIGN PATENT DOCUMENTS

| | | |
|---|---|---|
| EP | 0 747 703 A2 | 12/1996 |
| WO | WO 96/13609 | 5/1996 |
| WO | WO 99/06425 | 2/1999 |
| WO | WO 99/08717 | 2/1999 |
| WO | WO 99/43688 | 9/1999 |

OTHER PUBLICATIONS

Kawai et al Analytical Biochemistry vol. 209 pp. 63-69 1993.*
Kawai et al A Simple Method of Detecting Amplified DNA with Immobilized Probes on Microtiter Wells. 1992. vol. 209. pp. 63-69.*
Saiki et al. PNAS vol. 86, pp. 6230-6234 1989.*
International Search Report issued Feb. 28, 2003 for related, priority application EP 01 30 0630.

* cited by examiner

Primary Examiner—Jezia Riley
(74) Attorney, Agent, or Firm—Knobbe, Martens, Olson & Bear, LLP

(57) ABSTRACT

A nucleic acid to be immobilized and used for hybridization of nucleic acids using an immobilized nucleic acid, which has a polymer comprising a compound having an unsaturated bond, said polymer being bonded to the 3' end or 5' end or both ends of the nucleic acid; a nucleic acid-immobilized substrate comprising a substrate for immobilizing a nucleic acid and the polymer-having nucleic acid immobilized on the substrate; and a method for detecting a nucleic acid by hybridization using an immobilized nucleic acid, which comprises using the nucleic acid-immobilized substrate.

4 Claims, No Drawings

IMMOBILIZED NUCLEIC ACID AND METHOD FOR DETECTING NUCLEIC ACID

BACKGROUND OF THE INVENTION

The present invention relates to detection of a nucleic acid by hybridization. In particular, the present invention relates to a method for detecting a nucleic acid by hybridization as well as a nucleic acid and a nucleic acid-immobilized substrate used for the method.

In the fields of clinical test, food inspection, medicolegal test and so forth, as methods for detecting and identifying biologically active substances such as nucleic acids, antibodies and antigens present in specimens, nucleic acid probe methods, enzyme immunoassays and so forth are used depending on the target substance.

As methods utilizing detection of nucleic acids, there can be mentioned identification of microbial strains of pathogenic microbes etc., DNA identification in the medical jurisprudence and so forth. In these method, detection is usually carried out as follows. A nucleic acid having a sequence complementary to a target nucleic acid is labeled directly with an enzyme or the like, or labeled indirectly by using a hapten or the like. This labeled nucleic acid is hybridized with a target nucleic acid. After the labeled nucleic acid that does not hybridize is removed or its labeled portion is inactivated, the labeled portion of the hybridized target nucleic acid is detected to confirm presence and amount of the target nucleic acid.

In the conventional nucleic acid detection methods, it is extremely important to immobilize nucleic acids on a surface of solid phase such as tubes, microtiter plates, membrane filters and beads. Therefore, various methods have been published for immobilization of nucleic acids.

There are known, for example:

(1) a method of chemically bonding a nucleic acid into which a modification group is introduced, to a substrate, such as immobilization by a disulfide bond between a nucleic acid having a thiol group at its 5' end and a bead-like substrate having thiol groups (P. J. R. Day, P. S. Flora, J. E. Fox, M. R. Walker, Biochem. J., 278, 735–740 (1991));

(2) a method of attaining immobilization by physical adsorption, such as immobilization of nucleic acid by adsorption on nitrocellulose, poly-L-Lysine, nylon membrane or the like through UV irradiation or heat treatment (J. Sambrook, E. F. Fritsch and T. Maniatis, Molecular Cloning, Cold Spring Harbor Laboratory Press, Second Edition, pages 2.109–2.113 and pages 9.34–9.46, International Patent Publication in Japanese (Kohyo) No. 10-503841), and immobilization by physical adsorption on a microplate (G. C. N. Parry and A. D. B. Malcolm, Biochem. Soc. Trans., 17, 230–231 (1989));

(3) a method of synthesizing DNA on a substrate using a nucleotide bonded to a substrate (WO97/10365), and so forth.

However, these methods have drawbacks, i.e., in the method of (1), extremely special apparatuses and reagents are required, and in the method of (2), nucleic acids are dropped off from the substrate during the hybridization procedure, in particular, in operation processes, and thus detection sensitivity may be reduced or reproducibility may not be obtained. Furthermore, this method has another drawback, that is, although a long nucleic acid can be immobilized, a short nucleic acid of about 50-mer or less such as oligomers cannot be efficiently immobilized.

Further, in the method of (3), extremely special apparatuses and reagents are required for synthesizing DNA on a substrate, and the nucleic acid synthesized by this method is limited to about 25-mer or less.

SUMMARY OF THE INVENTION

An object of the present invention is to provide a method for easily and efficiently immobilizing a nucleic acid on a substrate in a simple manner, a method for detecting a nucleic acid by hybridization with high sensitivity using the method, and a nucleic acid and a nucleic acid-immobilized substrate used for the method.

The present inventors studied in order to achieve the aforementioned object. As a result, they found that a nucleic acid having a polymer comprising a compound having an unsaturated bond, the polymer being bonded to the 3' end or the 5' end or both ends of the nucleic acid, could be firmly immobilized even if the nucleic acid is short one, and if a substrate on which such a nucleic acid was immobilized was used, sensitivity of nucleic acid detection by hybridization could be improved. Thus, they accomplished the present invention.

That is, the present invention provides the followings.

(1) A nucleic acid to be immobilized and used for hybridization of nucleic acids using an immobilized nucleic acid, which has a polymer comprising a compound having an unsaturated bond, said polymer being bonded to the 3' end or the 5' end or both ends of the nucleic acid.

(2) The nucleic acid according to (1), wherein an average degree of polymerization of the polymer is not less than 3 and not more than 100.

(3) The nucleic acid according to (2), wherein a monomer which constitutes the polymer is nucleotide.

(4) A nucleic acid-immobilized substrate comprising a substrate for immobilizing a nucleic acid and the nucleic acid as defined in any one of (1) to (3) immobilized on the substrate.

(5) A method for producing a nucleic acid-immobilized substrate, comprising bringing a substrate for immobilizing a nucleic acid into contact with the nucleic acid as defined in any one of (1) to (3), and irradiating a contact portion with an electromagnetic wave.

(6) A method for detecting a nucleic acid by hybridization using an immobilized nucleic acid, which comprises using the nucleic acid-immobilized substrate as defined in (4).

According to the present invention, a nucleic acid that can be stably immobilized on a substrate or a carrier on a substrate can be provided. By adding a polymer to an end of an arbitrary nucleic acid, the amount of the arbitrary nucleic acid that can be immobilized on a substrate or a carrier on a substrate can be increased, and thus the detection sensitivity can be improved.

Further, since the polymer selectively reacts with the substrate or the carrier on the substrate, the nucleic acid detection can be performed without using nucleotides required for the hybridization in the arbitrary nucleic acid, for the immobilization on the substrate or the carrier on the substrate. This makes it possible to provide a nucleic acid detection method that can more selectively detect difference of nucleotide sequence.

Furthermore, because the nucleic acid can be more firmly bonded to the substrate or the carrier on the substrate, the nucleic acid-immobilized substrate can be a nucleic acid-immobilized substrate that is effective in use as DNA chips of superior reproducibility and quantification property and so forth.

DETAILED DESCRIPTION OF THE INVENTION

Embodiments of the present invention will be explained in detail hereafter.

<1> Nucleic Acid

The nucleic acid of the present invention is a nucleic acid having a polymer comprising a compound having an unsaturated bond, the polymer being bonded to the 3' end or the 5' end or both ends of the nucleic acid. That is, the nucleic acid of the present invention comprises a polymer portion and a portion comprising a region to be involved in hybridization (hereinafter also referred to as "specific region" for convenience). The portion comprising the specific region of the nucleic acid of the present invention is not particularly different from a usual immobilized (solid phase-immobilized) nucleic acid used for hybridization of nucleic acids using an immobilized nucleic acid except that it has the polymer bonded to its 3' end or 5' end or both ends, and it is not particularly limited so long as it is a nucleic acid that allows hybridization. For example, it may be a naturally occurring or synthesized DNA (including oligonucleotides) or RNA (including oligonucleotides). Further, it may be single-stranded or double-stranded. The length of the specific region is not also particularly limited so long as it allows hybridization. However, it is usually about 5 to 1,000,000 nucleotides, preferably 10 to 2000 nucleotides.

In order to bind the polymer to the 3' end or the 5' end or both ends of the portion comprising the specific region of nucleic acid, known methods can be used. Specific examples of the method include, for example, a method of synthesizing a nucleic acid so that it contains polymerized three or more nucleotides having nucleic acid bases such as thymine, uracil and the like as the compound constituting the polymer, at the 3' end or the 5' end or both ends of the portion comprising the specific region of the nucleic acid, as a single integrated nucleic acid by using a commercially available nucleic acid synthesizer.

The term "polymer comprising a compound having a unsaturated bond" means a polymer in which at least one of monomers constituting the polymer comprises a compound having an unsaturated bond. The compound having the unsaturated bond is sufficient to be so contained that the nucleic acid is immobilized on the nucleic acid-immobilizing substrate. It is preferred that each of monomers constituting the polymer comprises a compound having an unsaturated bond. The term "comprise a compound having an unsaturated bond" means to consist of a residue of a compound having an unsaturated bond or comprise the residue.

With respect to the length of the polymer, its average degree of polymerization is preferably 3 to 100, more preferably 5 to 50, particularly preferably 10 to 40.

If the average degree of polymerization is two or less, the nucleic acid may not be immobilized in a sufficient amount on a substrate or a carrier, and if the degree of polymerization is 101 or more, yield of the nucleic acid production process may be markedly reduced.

Specific examples of the polymer include those containing a monomer selected from a nucleotide having, as base, adenine, an adenine derivative, cytosine, a cytosine derivative, guanine, a guanine derivative, thymine, a thymine derivative, uracil, or a uracil derivative; an acrylic acid or methacrylic acid ester monomer; a styrene monomer; a polyolefin monomer; a vinyl monomer; a nitrile monomer; ethylene glycol diacrylate; ethylene glycol dimethacylate; tetraethylene glycol diacrylate; trimethylolpropane triacrylate; tetramethylolpropane tetraacrylate; dipentaerythritol pentaacrylate and the like. Monomers in the polymer may be identical or different from one another. A preferred monomer is a nucleotide.

When a nucleotide having a nucleic acid base is used as a monomer constituting the polymer, if a base of a kind different from that of the nucleic acid base is inserted into the polymer, cross-hybridization between the immobilized nucleic acid and a sample nucleic acid to be hybridized can be suppressed. For example, when a poly-T or poly-U is used as the polymer, if poly-A RNA is contained in the sample nucleic acid, it may cause hybridization regardless of the sequence of the specific region. Even in such a case, if a nucleotide having another base or a compound that does not form a base pair with any of bases is inserted into the poly-T or poly-U, cross-hybridization will be suppressed. Examples of such a compound include known compounds which can be inserted into polynucleotide such as nucleotides having adenine derivatives, cytosine derivatives, thymine derivatives, guanine derivatives, uracil derivatives and the like, deoxyribonucleic acids and ribonucleic acids that do not have a purine ring or pyrimidine ring, glucose, galactose, maltose, alkyl group-containing compounds, alkoxyl group-containing compounds, amino group-containing compounds, imino group-containing compounds, hydroxyl group-containing compounds, halogen-containing compounds, sulfonic acid-containing compounds, carboxylic acid-containing compunds, phosphonic acid-containing compounds and so forth. The length of the inserted nucleotides or compounds is usually 1 to 70 molecules. The inserted nucleotides or compounds may not be contiguous.

<2> Substrate for Immobilizing Nucleic Acid

The nucleic acid-immobilizing substrate used in the present invention is not particularly limited so long as it allows immobilization of a nucleic acid by physical adsorption or chemical bonding and can stantd conditions of usual hybridization. Specifically, it can be composed of a material that is insoluble in solvents used for immobilization and hybridization of nucleic acid and so forth, and present as solid or gel at an ordinary temperature or within a temperature range around it (for example, 0° C. to 100° C.). The expression of "the substrate is insoluble in solvents" means that it is substantially insoluble in various solvents such as aqueous solvents and organic solvents used in the steps where a carrier that has a group having ability to bind a nucleic acid, for example, a carbodiimide group, is carried on the substrate, then nucleic acids are immobilized, and subsequently it is used as DNA chips or the like.

Specifically, examples of the material of the substrate include plastics, inorganic polymers, metals, naturally occurring polymers, ceramics and so forth.

Specific examples of the plastics include polyethylene, polystyrene, polycarbonate, polypropylene, polyamide, phenol resin, epoxy resin, polycarbodiimide resin, polyvinyl chloride, polyvinylidene fluoride, polyethylene fluoride, polyimide, acrylate resin and so forth.

Specific examples of the inorganic polymers include glass, quartz, carbon, silica gel, graphite and so forth.

Specific examples of the metals include gold, platinum, silver, copper, iron, aluminum, magnet, paramagnet and so forth.

Examples of the naturally occurring polymers include polyamino acid, cellulose, chitin, chitosan, alginic acid, derivatives thereof and so forth.

Specific examples of the ceramics include apatite, alumina, silica, silicon carbide, silicon nitride, boron carbide and so forth.

As for the shape of the substrate, the substrate may be, for example, a film, flat panel, particle, molded product (bead, strip, well of multi-well plate, strip, tube, mesh, continuous foam, membrane, paper, needle, fiber, plate, slide, cell culture container etc.), latex, or the like. Size of these is not particularly limited.

When a nucleic acid is immobilized on the aforementioned substrate, the nucleic acid may be directly immobilized on the substrate, or a carrier may be carried on the substrate and the nucleic acid may be immobilized on the substrate via the carrier. As for the carrier, the carrier itself may have ability to bind to the nucleic acid, or it may be one that can immobilize the nucleic acid via a ligand that has ability to bind to the nucleic acid. The term "carried" used herein means that the carrier is not substantially dropped off from the substrate in various solvents such as aqueous solvents and organic solvents used in the steps of immobilization of a nucleic acid on the carrier, use of the nucleic acid-immobilized substrate as DNA chips or the like and other steps.

The carrier used for the present invention may be carried simply by physical adsorption, or chemically carried through a covalent bond or the like, so long as the carrier is carried on the substrate. The carrier may be carried on the whole surface of the substrate, or may be carried on a part of the surface, as required.

As the carrier, organic low molecular weight molecules, plastics, inorganic polymers, metals, naturally occurring polymers, ceramics and so forth may be used.

Specific examples of the organic low molecular weight molecules include carbodiimide group-containing compounds, isocyanate group-containing compounds, nitrogen yperite group-containing compounds, aldehyde-group-containing compounds, amino group-containing compounds and so forth.

Specific examples of the plastics include polyethylene, polystyrene, polycarbonate, polypropylene, polyamide, phenol resin, epoxy resin, polycarbodiimide resin, polyvinyl chloride, polyvinylidene fluoride, and polyethylene fluoride, polyimide, acrylate resin and so forth.

Specific examples of the inorganic polymers include glass, quartz, carbon, silica gel, graphite and so forth.

Specific examples of the metals include gold, platinum, silver, copper, iron, aluminum, magnet, paramagnet and so forth.

Examples of the naturally occurring polymers include polyamino acid, cellulose, chitin, chitosan, derivatives thereof and so forth.

Specific examples of the ceramics include apatite, alumina, silica, silicon carbide, silicon nitride, boron carbide and so forth.

Such a carrier is highly adhesive to the aforementioned substrate, and it is carried on the substrate by using this adhesive property. When the carrier is carried on the substrate by using physical adhesion, a typical form thereof is a coated film.

For providing a carrier carried on the substrate as a coated film, there can be used known methods such as spraying, dipping, brushing, stamping, vapor deposition, and coating using a film coater.

In order to provide carbodiimide groups (resin having them) on the whole surface of a glass substrate, for example, the glass substrate is first immersed for about 2 to 3 hours under a temperature condition of about 70 to 80° C. in a solution obtained by dissolving an amino-substituted organoalkoxysilane such as 3-aminopropyltriethoxysilane in a suitable solvent. Then, the substrate is taken out and washed with water, and the substrate is dried by heating at about 100 to 120° C. for about 4 to 5 hours. After the drying, the substrate is immersed in a suitable solvent. After addition of a carbodiimide resin, it is stirred for about 12 hours under a temperature condition of about 30 to 170° C., and then the substrate is washed. It is also possible to introduce nitrogen yperite groups on a surface of glass substrate through a reaction of the amino group of the aforementioned 3-aminopropyltriethoxysilane and a functional group in the nitrogen yperite groups other than a nucleic acid-binding group by using a suitable solvent.

Further, introduction of various functional groups on surfaces of the various materials mentioned above in the explanation of the substrate have been commonly performed as conventional practice, and methods therefor are also known. Therefore, when functional groups other than amino group are introduced on a glass substrate, or a substrate composed of a material other than glass is used, functional groups can also be introduced on a substrate surface by using such known methods.

Further, among the plastic substrates mentioned above as the substrates, there are those already having such functional groups as mentioned above. Such materials can be used as they are for the production of the carrier without introducing functional groups on the substrate surface. Into even such plastic substrates, functional groups may be further introduced to use the substrates for the production of the carrier.

A known photopolymerization initiator may be mixed to the carrier or the substrate or a material thereof. By mixing the photopolymerization initiator, reactivity during immobilization of a nucleic acid by irradiation with an electromagnetic wave such as ultraviolet light may be improved.

<3> Nucleic Acid-immobilized Substrate

By immobilizing the nucleic acid on a nucleic acid-immobilizing substrate, the nucleic acid-immobilized substrate of the present invention can be obtained. When the nucleic acid is immobilized, the nucleic acid is preferably immobilized in a plurality of dot-like areas on the substrate. The immobilization on dot-like areas means that the sites on which the nucleic acid is immobilized are sufficiently small with respect to the size of the substrate in such a degree that a plurality of the nucleic acid-immobilized sites can be provided. The shape of the dots is not particularly limited, and it can be arbitrarily selected depending on the way of use, purpose of use and so forth of the nucleic acid-immobilized substrate.

As the nucleic acid immobilized on the nucleic acid-immobilizing substrate, the nucleic acid explained in the above <1> can be used without particular limitation.

The nucleic acids immobilized in a plurality of dot-like areas of the nucleic acid-immobilized substrate of the present invention may be identical or different from one another. When different nucleic acids are used, geometrical arrangement of those nucleic acids and so forth may suitably be selected depending on the way of use, purpose of use and so forth of the nucleic acid-immobilized substrate to be obtained. The immobilized nucleic acid may be a mixture.

To immobilize such nucleic acids in dot-like shapes on the substrate or the carrier, small amounts of nucleic acids can be provided in dot-like shape of a desired size on the substrate or the carrier under a suitable condition so that the nucleic acids are brought into contact with the substrate or the carrier and immobilized.

Specifically, nucleic acids are usually provided in a state that they are contained in water or buffer so that the activity of the nucleic acids to be immobilized are maintained during the contact and the reaction of the both. The immobilization can also be attained by irradiation with an electromagnetic wave during or after the contact of the both. A known photopolymerization initiator may be mixed in the water or buffer.

The electromagnetic wave used for immobilization is preferably ultraviolet light having a wavelength of 220 nm to 380 nm. Its irradiation dose is preferably 10 to 5000 mJ/cm$^2$, more preferably 100 to 2000 mJ/cm$^2$. With respect to the shape of spectrum of irradiated ultraviolet light, one having a half-height width of not more than 100 nm is preferable, but it can be suitably selected depending on the shape of adsorption spectrum of the compound (polymer comprising a compound having an unsaturated bond).

Further, the immobilization can also be attained by contacting a mixture of the nucleic acid and a known compound such as carbodiimide resin, nitrogen yperite, polyamino acids and nitrocellulose, which are chemically bonded or physically associated, with a carrier. Also in such a case, the immobilization can also be attained by irradiation with the electromagnetic wave.

In the present invention, means for providing small amounts of nucleic acids, usually in the form of water or buffer containing the nucleic acids, in dot-like areas on the substrate or the carrier on the substrate includes a method of utilizing a dispenser, a method of utilizing a pin, a method of utilizing bubble jet and so forth. However, the present invention is not limited to these. Such apparatuses for providing solutions in small amounts are commercially available, and they can be used for the present invention.

When analysis is carried out by using the nucleic acid-immobilized substrate of the present invention, the substrate is frequently brought into contact with nucleic acids and so forth other than the aforementioned immobilized nucleic acids. Therefore, in order to prevent non-specific binding of the nucleic acids and so forth other than the immobilized nucleic acids to an unreacted portion for immobilizing nucleic acids, the unreacted portion for immobilizing nucleic acids are preferably blocked by bringing the substrate or the carrier on the substrate into contact with an excessive amount of bovine serum albumin (BSA), casein, salmon sperm DNA or the like, after the nucleic acids are immobilized in dot-like areas on the substrate or the carrier on the substrate as described above.

In the nucleic acid-immobilized substrate of the present invention obtained as described above, the nucleic acids are very firmly carried by the substrate or the carrier, and they are not released even by washing methods widely used for hybridization and so forth (washing methods using surfactants). If analysis is carried out by using it, the analysis can be performed with superior reproducibility and quantification ability. Further, since nucleic acids can be immobilized on the nucleic acid-immobilized substrate of the present invention irrespective of the number and length of the chains, various nucleic acids can be simultaneously dealt with on the same substrate.

Based on these facts, the nucleic acid-immobilized substrate of the present invention can be used as DNA chips (DNA microarrays) and so forth for techniques of determining nucleotide sequences by hybridization using a large number of nucleic acids, for example, SBH (Sequencing By Hybridization) method, SHOM (Sequencing by Hybridization with Oligonucleotide Matrix) method and so forth with superior performance.

Furthermore, the nucleic acid-immobilized substrate of the present invention can also be suitably used for recovery of nucleic acids by hybridization.

EXAMPLES

Hereafter, the present invention will be explained with reference to the following examples.

Preparation Example: Preparation of Carbodiimidated Slide Glass (1) Preparation of Aminated Slide Glass In an amount of 20 ml of 10% (v/v) solution of 3-aminopropyltriethoxysilane in ethanol was added to 180 ml of distilled water and stirred. After 6 N HCl was added to the solution to adjust pH of the solution to 3 to 4, 15 pieces of slide glass were immersed into the solution and heated at 75° C. for 2 hours. After the heating was finished, the slide glass was pulled up from the solution, and the solution was sufficiently washed down with distilled water. Then, the slide glass was subjected to a heat treatment at 115° C. for 4 hours to obtain aminated slide glass.

(2) Preparation of Carbodiimide Resin

In an amount of 12.5 g of cyclohexyl isocyanate (Tokyo Kasei Kogyo) and 1.3 g of 3-methyl-1-phenyl-2-phospholene-1-oxide (Aldrich) were added to 117.9 g of hexamethylene diisocyanate (Aldrich). Then, the mixture was stirred at 185° C. for 96 hours, while nitrogen was added to the mixture at a flow rate of 0.5 ml/minute. After cooling, carbodiimide resin was obtained as powder. The average degree of polymerization of the obtained resin was 10, and the number average molecular weight was 2400.

(3) Preparation of Carbodiimidated Slide Glass

A 10% solution of the carbodiimide resin prepared in the above (2) in chloroform was prepared, and 15 pieces of the aminated slide glass prepared in the above (1) were immersed in the solution and immediately pulled up. Then, the slide glass was washed twice with 200 ml of chloroform for 10 minutes, and dried at 40° C. for 2 hours to obtain carbodiimidated slide glass.

Example 1

(1) Immobilization of Nucleic Acid Having Polymerized Nucleotides at End

An oligonucleotide (31-mer) having the nucleotide sequence shown in SEQ ID NO: 1 was dissolved in 2 M NaCl at a concentration of 100 ng/μl to obtain a DNA solution. The DNA solution was spotted on 500 predetermined positions of the carbodiimidated slide glass obtained in the above Preparation Example by using a spotter (SP-BIO: Hitachi Software Engineering). The slide glass was put into a dryer and dried for at 37° C. for 15 minutes. Then, the slide glass was immersed in Buffer A (0.2 M sodium chloride, 0.1 M Tris-HCl (pH 7.5), 0.05% Triton X-100) containing 3% BSA (bovine serum albumin), and dried at 37° C. for 15 minutes. Subsequently, this slide glass was washed with TE buffer (10 mM Tris-HCl, pH 7.2/1 mM EDTA) and dried at 37° C. for 15 minutes.

Separately, an oligomer that did not show complementarity to the probe mentioned hereinafter at all (SEQ ID NO: 3) was similarly immobilized on the carbodiimidated slide glass as a control.

(2) Hybridization

On each of the DNA-immobilized portions of the aforementioned slide glass, a hybridization solution [3×SSC (SSC: 1.5 M NaCl, 0.15 M sodium citrate), 10% dextran, 1 pmol of biotinylated probe] 30 μl was placed, and heated overnight on a water bath at 42° C. As the probe nucleic acid, Shiga-like toxin type 2 gene derived from a Shigella bacterium was amplified by PCR by using a probe labeled with biotin, and the obtained amplification product (about 1.2 kb) was used.

(3) Post-hybridization

After the hybridization, the hybridization solution was lightly absorbed from the slide glass, and the slide glass was subjected to post-hybridization washing under the following conditions to remove non-specifically adsorbed probe.

[Post-hybridization Washing Solution and Condition]
(i) 2×SSC, 1% SDS; room temperature, 5 minutes, 2 times
(ii) 0.2×SSC, 1% SDS; 40° C., 5 minutes, 2 times
(iii) 2×SSC; room temperature, 5 minutes, once (4) Detection of Hybridization The slide glass after the aforementioned post-hybridization washing was subjected to blocking by immersing it in Buffer A (500 ml) containing 3% BSA at room temperature for 30 minutes. Then, it was immersed in 45 ml of a solution of streptavidin-alkaline phosphatase conjugate (prepared by diluting 2000 times a stock solution (Boehringer Mannheim) with Buffer A having the composition described below and containing 3% BSA) and allowed to react at room temperature for 30 minutes. Then, the slide glass was immersed in Buffer A (50 ml) and left at room temperature for 5 minutes. This procedure was repeated twice to remove the conjugate not bound to the biotin. Then, the slide glass was washed once with Buffer B (30 ml) having the composition described below. Finally, it was immersed in a substrate solution (20 ml of Buffer B, 18 μl of BCIP (5-bromo-4-chloro-3-indolyl phosphate) solution, 36 μl of NBT (nitroblue tetrazolium) solution and left at room temperature for 3 hours to perform the color development reaction. The result is shown in Table 1.

[Composition of Buffer A]
0.2 M NaCl
0.1 M Tris-HCl (pH 7.5)
0.05% Triton X-100

[Composition of Buffer B]
0.1 M NaCl
0.1 M Tris-HCl (pH 9.5)

Comparative Example 1

Hybridization and color development reaction were performed in the same manner as in Example 1 except that an oligonucleotide (21-mer) having the nucleotide sequence shown in SEQ ID NO: 2 was used instead of the oligonucleotide (31-mer) having the nucleotide sequence shown in SEQ ID NO: 1 in (1) to (4) of Example 1. The result is shown in Table 1.

TABLE 1

| | Signal detection |
|---|---|
| Example 1 | ⊙ |
| Comparative Example 1 | ○ |

⊙: Most of signals appeared extremely clearly with extremely high sensitivity.
○: Most of signals appeared clearly with high sensitivity.

From the results shown in Table 1, it can be seen that detection of nucleic acid appears as an extremely clear signal with extremely high sensitivity according to the nucleic acid detection method of the present invention.

Separately, an oligomer that does not have complementarity to the aforementioned probe at all was also immobilized in a similar manner as a control. In such a case, no signal appeared at all in the both of the procedures of Example 1 and Comparative Example 1.

Example 2

(1) Immobilization of Nucleic Acid Having Polymerized Nucleotides at End

Oligonucleotides (18-mer to 28-mer) having the nucleotide sequences shown in SEQ ID NOS: 4 to 12 were each dissolved in 2 M NaCl at a concentration of 100 ng/μl to obtain DNA solutions. Each of the DNA solutions was spotted on two predetermined positions of the carbodiimidated slide glass obtained in the above Preparation Example by using a spotter (GT MASS: Nippon laser Denshi). It was then subjected to UV irradiation (wavelength: 254 nm, dose: 600 mJ/cm$^2$) with UV STRACTLINKER™. The slide glass was immersed in Buffer A (0.2 M sodium chloride, 0.1 M Tris-HCl (pH 7.5), 0.05% Triton X-100) containing 3% BSA (bovine serum albumin), and dried at 37° C. for 15 minutes. Subsequently, this slide glass was washed with TE buffer (10 mM Tris-HCl, pH 7.2/1 mM EDTA) and dried at 37° C. for 15 minutes.

(2) Hybridization

On each of the DNA-immobilized portions of the aforementioned slide glass, a hybridization solution [3×SSC (SSC: 1.5 M NaCl, 0.15 M sodium citrate), 10% dextran, 1 pmol of Cy5-labeled probe] 30 μl was placed, and heated overnight on a water bath at 42° C. As the probe nucleic acid, RNA polymerase β subunit gene (rpoB) was amplified by PCR by using a probe labeled with Cy5, and the obtained amplification product (about 110 b) was used.

(3) Post-hybridization

After the hybridization, the hybridization solution was lightly absorbed from the slide glass, and the slide glass was subjected to post-hybridization washing under the following conditions to remove non-specifically adsorbed probe.

[Post-hybridization Washing Solution and Condition]
(i) 2×SSC, 0.1% SDS; room temperature, 5 minutes, 2 times
(ii) 0.3×SSC, 0.1% SDS; 40° C., 5 minutes, 2 times
(iii) 2×SSC; room temperature, 5 minutes, once (4) Detection of Hybridization The obtained slide glass was measured with SCAN ARREY (GSI). The results are shown in Table 2. The Sequences 4 to 12 are the nucleotide sequences shown in SEQ ID NOS: 4 to 12, respectively. The features thereof are as follows: Sequence 4: a complementary chain in which T bases are added to its terminal; Sequences 5 to 7: negative controls in which T bases are added to their terminals; Sequence 8: a complementary chain in which T bases are not added to its terminal; Sequences 9 to 11: negative controls in which T bases are not added to their terminals; Sequence 12: a positive control (a complementary chain different from that of Sequence 4, in which T bases are added to its terminal).

TABLE 2

| Sequence | Signal detection |
|---|---|
| Sequence 12 | ⊚ |
| Sequence 4 | ⊚ |
| Sequence 5 | X |
| Sequence 6 | X |
| Sequence 7 | X |
| Sequence 8 | ○ |
| Sequence 10 | X |
| Sequence 11 | X |

⊚: An extremely strong signal was observed.
○: A signal was observed.
X: No signal was observed.

From the results shown above, it can be seen that detection of nucleic acid appears as an extremely clear signal with extremely high sensitivity according to the nucleic acid detection method of the present invention.

Example 3

(1) Immobilization of Nucleic Acid Having Polymerized Nucleotides at End

ECH-modified glycerol triacrylate (Nagase Sangyo) was treated with methyltrimethoxyphosphonium iodide (Aldrich) in DMF to iodinate hydroxy groups of ECH-modified glycerol triacrylate. Then, the obtained compound was reacted with each of oligonucletides (18-mer) having the nucleotide sequences shown in SEQ ID NOS: 13 to 17, of which 5' end is modified with an $NH_2$ group, in a weak alkaline solution by heating. Introduction of ECH-modified glycerol triacrylate into the resultant oligonucleotides was confirmed by using HPLC.

ECH-modified glycerol triacrylate-introduced oligonucleotides were each dissolved in 2 M NaCl/DMSO at a concentration of 100 ng/μl to obtain DNA solutions. Each of the DNA solutions was spotted on two predetermined positions of the carbodiimidated slide glass obtained in the above Preparation Example by using a spotter (GT MASS: Nippon laser Denshi). It was then subjected to UV irradiation (wavelength: 254 nm, dose: 1200 $mJ/cm^2$) with UV STRACTLINKER™. The slide glass was immersed in Buffer A (0.2 M sodium chloride, 0.1 M Tris-HCl (pH 7.5), 0.05% Triton X-100) containing 3% BSA (bovine serum albumin), and dried at 37° C. for 15 minutes. Subsequently, this slide glass was washed with TE buffer (10 mM Tris-HCl, pH 7.2/1 mM EDTA) and dried at 37° C. for 15 minutes.

(2) Hybridization

On each of the DNA-immobilized portions of the aforementioned slide glass, a hybridization solution [3×SSC (SSC: 1.5 M NaCl, 0.15 M sodium citrate), 10% dextran, 1 pmol of Cy5-labeled probe] 30 μl was placed, and heated overnight on a water bath at 42° C. As the probe nucleic acid, RNA polymerase β subunit gene (rpoB) was amplified by PCR by using a probe labeled with Cy5, and the obtained amplification product (about 110 b) was used.

(3) Post-hybridization

After the hybridization, the hybridization solution was lightly absorbed from the slide glass, and the slide glass was subjected to post-hybridization washing under the following conditions to remove non-specifically adsorbed probe.

[Post-hybridization Washing Solution and Condition]
(i) 2×SSC, 0.1% SDS; room temperature, 5 minutes, 2 times
(ii) 0.3×SSC, 0.1% SDS; 40° C., 5 minutes, 2 times
(iii) 2×SSC; room temperature, 5 minutes, once (4) Detection of Hybridization The obtained slide glass was measured with SCAN ARREY (GSI). As a result, strong signals were observed only on SEQ ID NOS: 13 and 17 as in Examples 2. The features of the nucleotide sequences shown in SEQ ID NOS: 13 to 17 are as follows: SEQ ID NO: 13: a complementary chain; SEQ ID NOS: 14 to 16: negative controls; SEQ ID NO: 17: a positive control (a complementary chain different from that of SEQ ID NO: 13).

It can be seen that detection of nucleic acid appears as an extremely clear signal with extremely high sensitivity according to the nucleic acid detection method of the present invention.

What is claimed is:

1. A nucleic acid-immobilized substrate comprising a substrate and a nucleic acid immobilized on the substrate, wherein
   (1) the substrate consists of a plastic selected from the group consisting of polyethylene, polystyrene, polycarbonate, polypropylene, phenol resin, epoxy resin, polycarbodiimide resin, polyvinyl chloride, polyvinylidene fluoride, polyethylene fluoride, polyimide, and acrylate resin, or the substrate carries a carrier thereon, said carrier consisting of the plastic;
   (2) the nucleic acid has a polymer comprising a compound having an unsaturated bond, said polymer being bonded to the 3' end or 5' end or both ends of the nucleic acid, said polymer being a polymer of a monomer having a base selected from the group consisting of thymine, a thymine derivative, uracil and a uracil derivative, with an average degree of polymerization of the polymer being not less than 3 and not more than 100; and
   (3) the nucleic acid-immobilized substrate is obtained by bringing the substrate into contact with the nucleic acid, and irradiating a contact portion with an electromagnetic wave, whereby the polymer reacts with the plastic.

2. A method for producing a nucleic acid-immobilized substrate, comprising bringing a substrate into contact with a nucleic acid, and irradiating a contact portion with an electromagnetic wave, wherein
   (1) the substrate consists of a plastic selected from the group consisting of polyethylene, polystyrene, polycarbonate, polypropylene, phenol resin, epoxy resin, polycarbodiimide resin, polyvinyl chloride, polyvinylidene fluoride, polyethylene fluoride, polyimide, and acrylate resin, or the substrate carries a carrier thereon, said carrier consisting of the plastic; and
   (2) the nucleic acid has a polymer comprising a compound having an unsaturated bond, said polymer being bonded to the 3' end or 5' end or both ends of the nucleic acid, said polymer being a polymer of a monomer having a base selected from the group consisting of thymine, a thymine derivative, uracil and a uracil derivative, with an average degree of polymerization of the polymer being not less than 3 and not more than 100, and whereby the polymer reacts with the plastic.

3. A method for detecting a nucleic acid by hybridization using an immobilized nucleic acid, which comprises hybridizing the nucleic acid to be detected to the nucleic acid-immobilized substrate as defined in claim 1.

4. The method according to claim 3, further comprising: washing the nucleic acid-immobilized substrate; and detecting the hybridized nucleic acid.

* * * * *

UNITED STATES PATENT AND TRADEMARK OFFICE
CERTIFICATE OF CORRECTION

PATENT NO. : 7,037,649 B2
APPLICATION NO. : 09/771043
DATED : May 2, 2006
INVENTOR(S) : Kimura et al.

It is certified that error appears in the above-identified patent and that said Letters Patent is hereby corrected as shown below:

Column 1, Line 20, "In these method," should be changed to --In these methods,--

Column 4, Line 32, "acid-containing compunds," should be changed to --acid-containing compounds--

Column 4, Line 41, "and can stantd:" should be changed to --and can stand--

Column 17, Line 40, "wherein" should be changed to --wherein:--

Column 18, Line 38 "wherein" should be changed to --wherein:--

Signed and Sealed this

Twenty-first Day of November, 2006

JON W. DUDAS
*Director of the United States Patent and Trademark Office*

SEQUENCE LISTING

```
<160> NUMBER OF SEQ ID NOS: 17

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1 ttttttttt gttacccaca taccacgaat c                                      31

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
```
gttacccaca taccacgaat c                                          21

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
tttttttttt ttcttctcag tgcgcaaatt                                 30

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
tttttttttt aattcatggt ccagaaca                                   28

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
tttttttttt aattcatgga ccagaaca                                   28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
tttttttttt aattcatggg ccagaaca                                   28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
tttttttttt aattcatggc ccagaaca                                   28

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
aattcatggt ccagaaca                                        18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
aattcatgga ccagaaca                                        18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
aattcatggg ccagaaca                                        18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
aattcatggc ccagaaca                                        18

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
tttttttttt agctgagcca attcatgg                             28

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
aattcatggt ccagaaca                                        18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
aattcatgga ccagaaca                                        18

```
<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
aattcatggg ccagaaca                                                 18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
aattcatggc ccagaaca                                                 18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
agctgagcca attcatgg                                                 18
```